United States Patent [19]

De Jager

[11] Patent Number: 5,205,327
[45] Date of Patent: Apr. 27, 1993

[54] ELECTROSTATIC WEFT DETECTOR

[75] Inventor: Godert De Jager, Benglen, Switzerland

[73] Assignee: Sulzer Brothers Limited, Winterthur, Switzerland

[21] Appl. No.: 860,746

[22] Filed: Mar. 25, 1992

[30] Foreign Application Priority Data

May 15, 1991 [CH] Switzerland .................. 01449/91-0

[51] Int. Cl.$^5$ ............................................. D03D 51/34
[52] U.S. Cl. ............................. 139/370.1; 139/370.2; 340/677; 324/662
[58] Field of Search .............. 66/163; 340/677; 57/81; 139/370.1, 370.2, 192; 324/662, 671, 687, 688; 73/160; 361/321, 283

[56] References Cited

U.S. PATENT DOCUMENTS

| | | | |
|---|---|---|---|
| 4,311,958 | 1/1982 | Aeppli | 324/671 |
| 4,766,368 | 8/1988 | Cox | 324/662 X |
| 5,027,253 | 6/1991 | Lauffer et al. | 361/321 |
| 5,083,584 | 1/1992 | Weidmann et al. | 139/370.2 |

FOREIGN PATENT DOCUMENTS

| | | |
|---|---|---|
| 0036314 | 9/1981 | European Pat. Off. . |
| 2140812 | 2/1973 | Fed. Rep. of Germany . |
| 2435375 | 2/1975 | Fed. Rep. of Germany . |
| 2758403 | 7/1978 | Fed. Rep. of Germany . |
| 2125156 | 9/1972 | France . |
| 2376058 | 7/1978 | France . |
| 1528826 | 12/1989 | U.S.S.R. .................. 139/370.1 |

Primary Examiner—Andrew M. Falik
Attorney, Agent, or Firm—Townsend and Townsend, Khourie and Crew

[57] ABSTRACT

The weft break stop motion (1) detects without contact a potential displacement in the feeler (5a) effected by a weft thread moving past by means of a plate-like layered sensor element (2). With the feeler (5a) turned towards the weft thread insertion, the sensor element (2) can be introduced between the drop wires (23) of the reed (18). The weft break stop motion (1) and the sensor element (2) can be variably positioned along the reed (18), depending on the screen of the drop wires (23), and is normally placed directly outside the warp threads according to the loom width.

20 Claims, 3 Drawing Sheets

ELECTROSTATIC WEFT DETECTOR

BACKGROUND OF THE INVENTION

The invention relates to a weft stop motion, or detector, for looms in which the sensor element responds or is sensitive to an electric charging of the weft thread without contact and also to looms in which the weft break stop motion of the present invention is used.

A concept for thread detection is known from German Patent Specification 3,758,403, for example. Various embodiments of electrostatic transformers are disclosed therein. These sensors are mainly used in air-jet looms. The weft thread is electrically charged during its removal from the weft thread supply because of the resultant friction and also during the weft insertion because of friction with the air. The electrostatic detection registers the presence of a textile fiber which is moving past and is electrically charged in this way, and the passage of the tip of an inserted weft thread in particular can also be detected. Weft break stop motions are used in the weft channel of the loom. The known embodiments are relatively large and heavy and are frequently constructed in the form of a confusor drop wire. The high-speed air-jet looms having a correspondingly high beat-up speed of the reed which are commonly used nowadays produce high vibration and acceleration loads on the known weft break stop motions, so that the known embodiments are no longer suitable for use on air-jet looms or the resultant electrical signals are very noisy.

SUMMARY OF THE INVENTION

The object of the invention is to produce a contact-free weft thread detector based on a capacitative type sensor, which is particularly suitable for use with high-speed air-jet looms.

The weft thread detector detects without contact a change in the potential effected by a passing weft thread by means of a sensor element layered like a plate. With the feeler turned towards the weft thread insertion, the sensor element can be inserted between the drop wires of the reed. The weft break stop motion and the sensor element can be positioned variably along the reed, independently of the screen of the drop wires, and is normally placed directly outside the warp wires according to the loom width.

The sensor element is constructed from plate-like layers having a low mass. The two most outer supported layers are electrically conductive and serve to screen electrical fields. Between them there is a plate-like layer of insulating material and in the middle there is the actual feeler, a plane electric conductor preferably formed as an open loop. The sensor element, especially the layers of the feeler, is preferably perpendicular to the weft insertion direction. The edge of the sensor element close to the weft channel preferably follows the contours of the weft channel in the reed, such as, for example, the contours of a profiled reed. The sensor element can be inserted between the drop wires of the reed, as a result of which there is support for the sensor element with respect to the forces, vibrations and acceleration load acting in the direction of the weft channel. The rigid, low-mass, laminated construction is dimensionally stable, prevents reciprocal relative movements of the plate-like conductive layers and thus reduces the noise of the electrical signal occurring in the event of high vibrational and acceleration loads, which is caused by changes in capacitance.

The entire weft stop motion is preferably constructed as a multi-layer plate, and it is also possible for the middle conductive layer together with the feeler to have further strip conductors for electronic components, especially a charge amplifier. The sensor element can be produced very cheaply. If an integrated switching circuit, such as, for example, a charge amplifier, is directly mounted on the middle layer, then it is possible to provide a very thin weft stop motion, which is electrically shielded by the two outer, overlapping plate-like conductive layers. If larger components are used as electronic components, the strip conductors can also be formed from a sub-region of the outermost electrically conductive layer of the weft stop motion and the electronic components can be mounted thereon. In addition a metal housing, which shields the electronic components and also the strip conductors from the outside, is also required.

The weft stop motion can be attached to the reed or loom sley by an attachment device. It is preferably inserted between the drop wires of the reed and can be variably positioned along the reed, independently from the screen of the drop wires, so that the sensor element comes to lie outside the loom width. The reed can therefore be kept at the original length for different loom widths and the sensor can be positioned so that it directly abuts the warp threads, for example outside the present loom width. The sensor can therefore be brought into an optimal position along the reed depending on the width of the woven goods.

The invention has the advantage that it is to a large extent possible to dispose the weft stop motion along the reed as desired without altering the functional design of the loom.

A further advantage of the sensor element of the present invention is that it is not sensitive to soiling.

DESCRIPTION OF THE PREFERRED EMBODIMENTS

Figure 1:
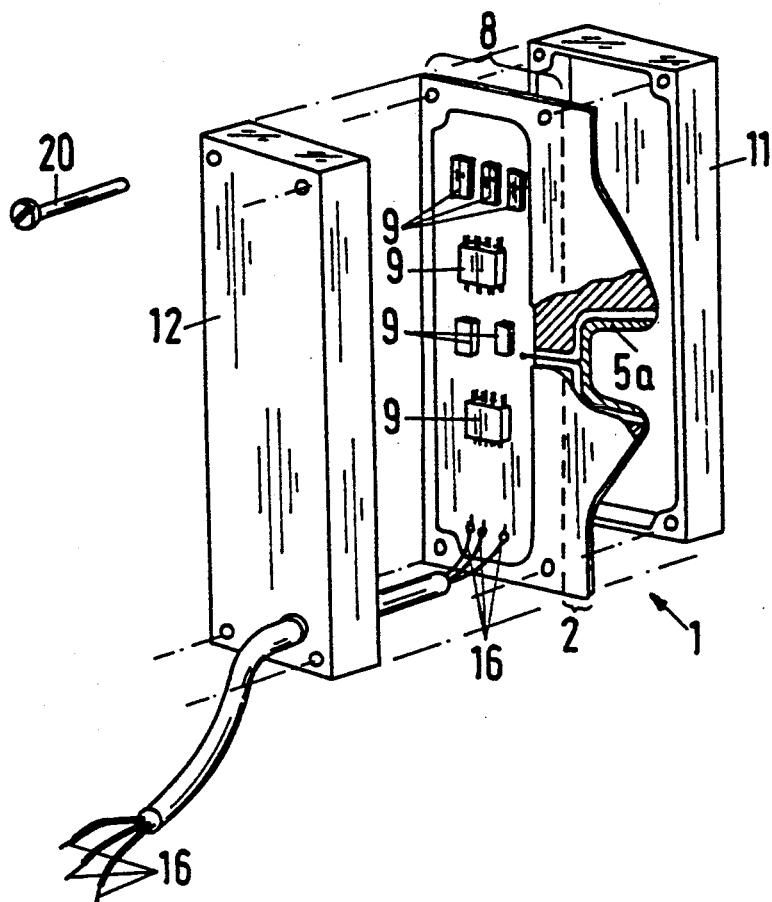
FIG. 1 shows a perspective view of a weft break stop motion exploded in the direction of the weft channel.

FIG. 1 shows a perspective view of the weft stop motion or detector 1 with its components. The weft stop motion 1 contains a sensor element 2 and also a board 8 for electronic components 9. Electrically conductive housing lids 11, 12 protect the interior of the weft break stop motion 1 surrounded thereby from electrical fields and mechanical effects and, together with the attachment means 20 constructed as screws and also an attachment device 15, enable the weft stop motion 1 to be fixed to the loom sley 22 or to the reed 18.

Figure 2:
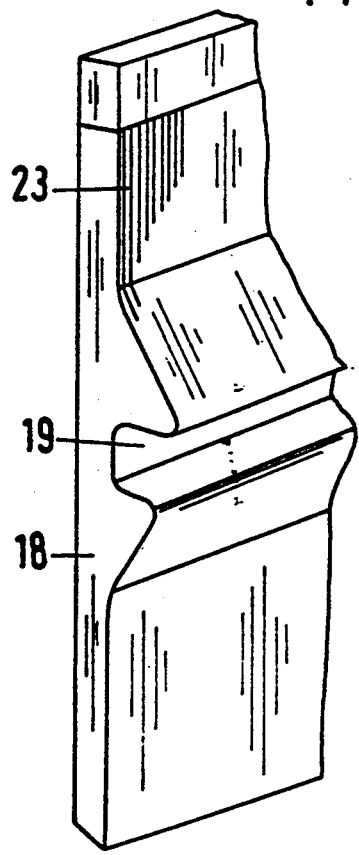
FIG. 2 shows a diagrammatic detail of a reed in an air-jet loom to illustrate the position of the weft break stop motion in the profiled reed.

FIG. 2 shows a reed 18 which is normally constructed from the drop wires 23 shown. The reed of an air-jet loom having an integrated weft channel 19 is shown as an example.

Figure 3:
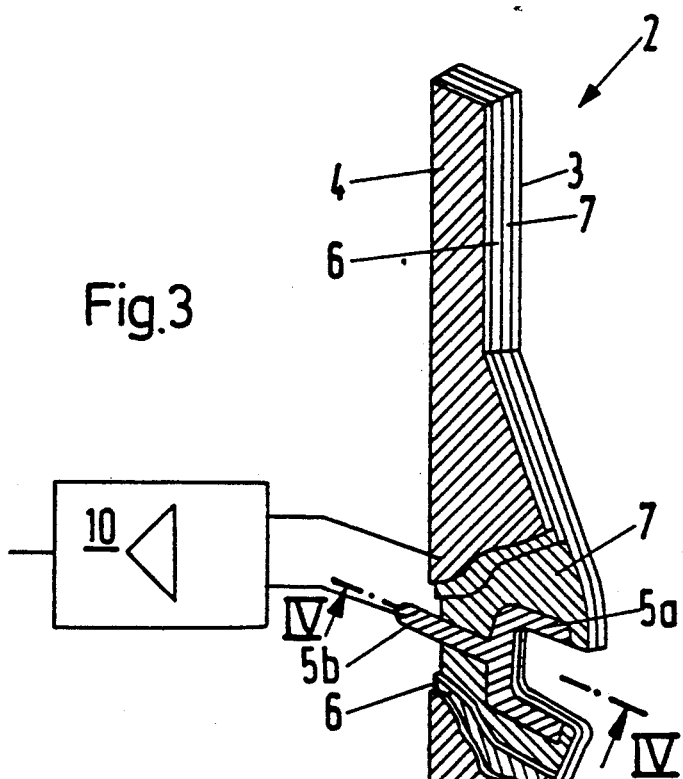
FIG. 3 shows a perspective detail of a sensor element according to FIG. 1.

In FIG. 3 the feeler 5a of the sensor 2 detects the relatively small potential fluctuations which occur through the electrically charged thread as it passes the feeler 5a. A shielded electrically conductive connection 5b supplies the detected signal to a charge amplifier 10. The components following the charge amplifier 10 for the further preparation and processing of the signals are not shown.

Figure 4:
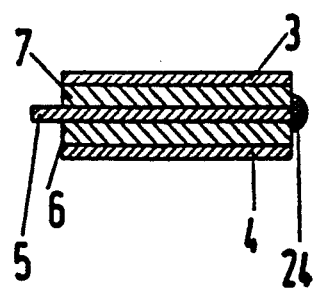
FIG. 4 shows a diagrammatic cross section through the sensor element in FIG. 3 to illustrate the stratified construction.

In FIG. 4 the sensor element 2 is constructed from plate-like layers. A middle electrically conductive layer 5 is surrounded on both sides by an insulating layer 6, 7 respectively, on which in turn there is an electrically conductive layer 3 or 4. The three electrically conductive layers 3, 4 and 5 are thin metal layers with a thickness in the micrometer range, with the outer layers 3 and 4 being grounded so as to shield the electrical conductors and connections formed with the layer 5 from external electrical fields. The insulating layers 6 and 7 are preferably substantially thicker than the electrically conductive layers 3, 4 and 5 so as to achieve a rigid mechanical sandwich construction.

The sensor element shown in FIG. 3 is designed so that it can be inserted between the drop wires 23 of the reed 18 and has thicknesses of less than 1 mm. The edge of the sensor element 2 close to the weft channel 19 of the profiled reed 18 follows the contours of the reed 18. The laminated construction of the sensor element 2 is achieved with a multi-layer printed circuit board, for example. The middle electrically conductive layer 5 of the sensor element 2 is preferably made from a metal, such as copper, for example, and has a thickness of a few micrometers. The actual feeler 5a is constructed as an open loop in the present exemplified embodiment from this electrically conductive layer 5, with the feeler 5a surrounding the weft channel 19 inside the profiled reed 18 so that the cross section of the weft channel 19 is not reduced by the sensor element 2. Of course the feeler 5a can naturally be constructed with different shapes, thus, for example, only with the lower half of the shape shown in FIG. 3. Together with the feeler 5a, the middle layer 5 comprises a conductive connection 5b from the feeler 5a to a charge amplifier 10. Further conductive connections or shielding, grounded layers can be formed from the middle layer 5. In FIG. 3 the feeler 5a is disposed so that the side close to the weft channel 19 is electrically conductive with respect to the outside. The feeler 5a can also be integrated in the sensor element 2 so that on the side of the weft channel there is an electrically insulating layer between the weft channel 19 and the feeler 5a. As a result the feeler becomes less sensitive to soiling. To increase the sensitivity of the sensor, an electrical conductor 24, which is only connected to the feeler 5a in an electrically conductive manner, can be mounted on the edge close to the weft thread. The sensor element 2 and the support 8 can be combined as a cohesive unit if both parts have the same plate-like structure and consequently form a single part.

Figure 5:
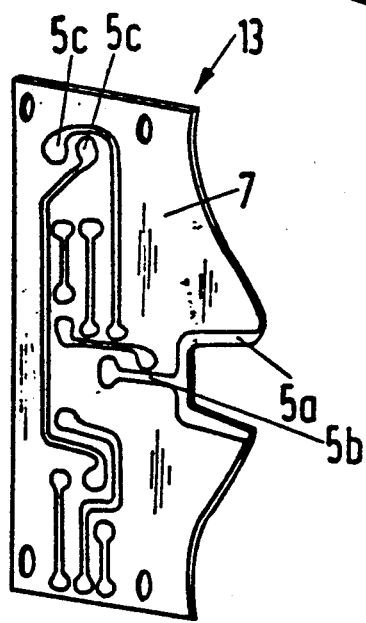
FIG. 5 shows a diagrammatic view of the middle conductive layer of the sensor element.

FIG. 5 shows a printed circuit board 13 from the middle conductive layer 5 of which the strip conductors 5c, the conductive connection 5b and also the sensor 5a were formed. The electronic components 9 are preferably mounted on the printed circuit board 13 using SMD technology so as to avoid holes for their connection. The integrated switching circuits are directly mounted on the insulating layer 7 and connected to the strip conductors 5c. For flat electronic components located inside the insulating layer 6, there is a flat weft stop motion 1, in which, the electronic components 9, 10 are electrically shielded by the outer conductive layers 3 and 4. The strip conductors 5c may also be formed from a sub-region of the outermost layer 4 of the support 8. The conductive connection 5b is through-plated to the strip conductors 5c. The electrical shielding of the electronic components 9, 10 is achieved by additional electrically conductive housing lids 11 and 12. An electrical connection 16 conveys the signal from the feeler 5a amplified at least with one charge amplifier towards the outside.

Figure 6:
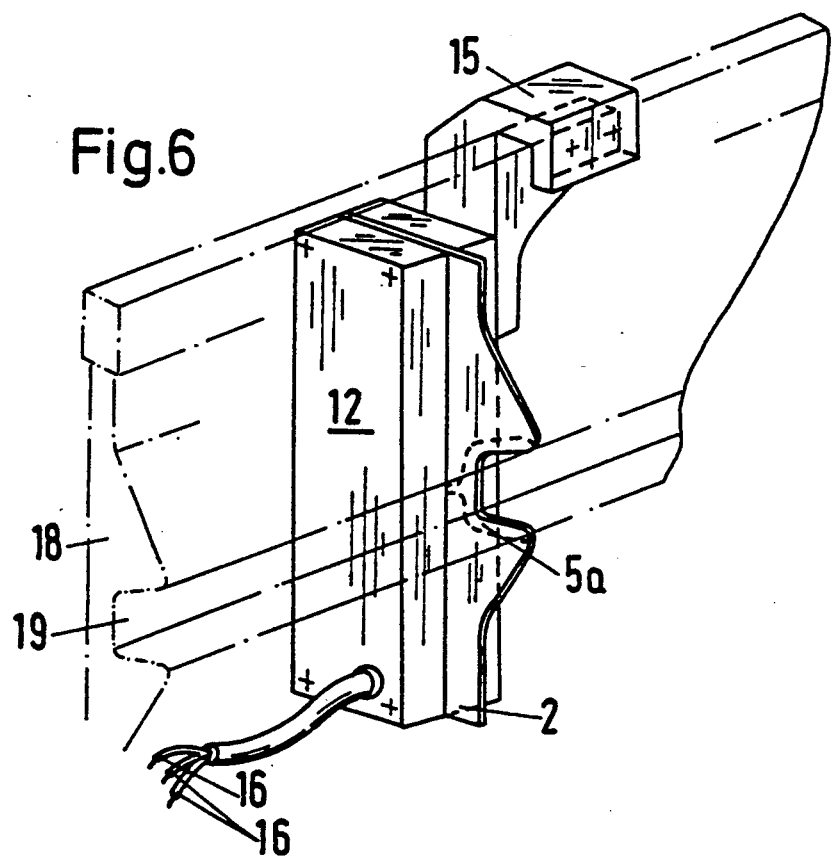
FIG. 6 diagrammatically shows the perspective view of a weft break stop motion with an attachment device on the reed.

In FIG. 6 the weft stop motion 1 is detachably fixed with attachment means 20 to the reed 18 or to the loom sley 22 and with the sensor 5a penetrates the drop wires. It can be variably positioned along the reed 18, with the weft stop motion 1 and also the sensor element 2 lying outside the loom width and not touching any warp threads.

Figure 7:
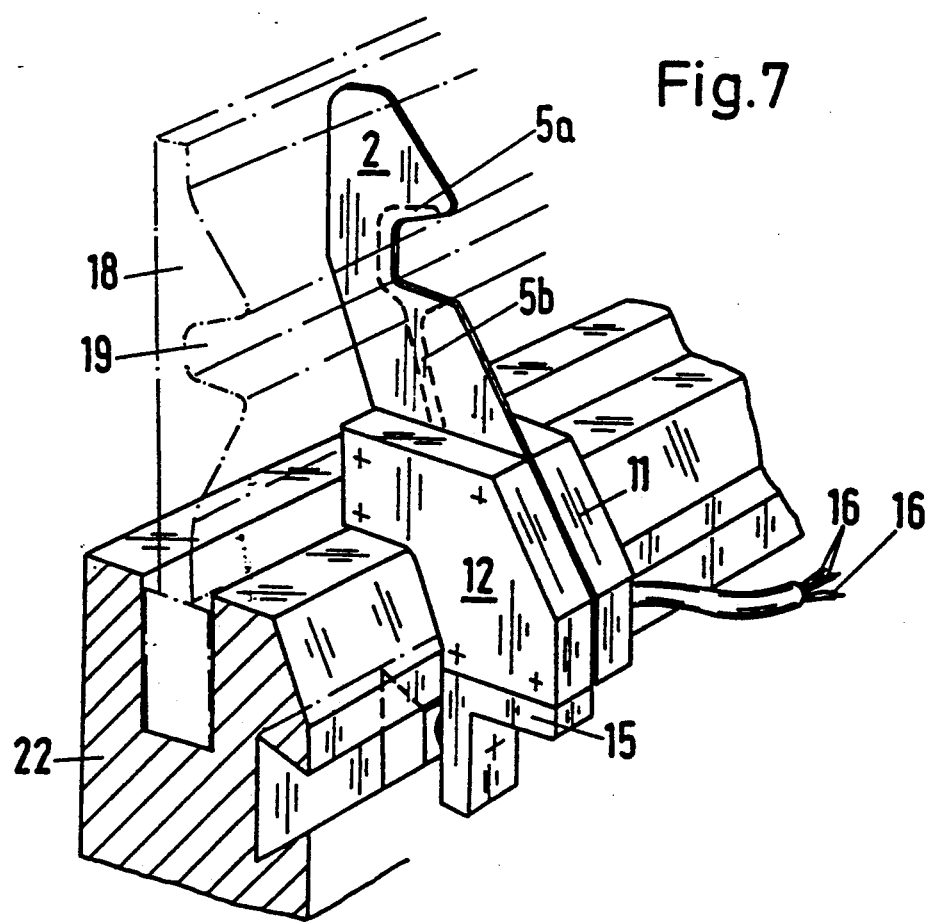
FIG. 7 diagrammatically shows the perspective view of a weft break stop motion with attachment to the loom sley.

FIG. 7 shows a further embodiment of a weft stop motion 1 having an attachment device 15. By extending the conductive connection 5b between feeler 5a and the charge amplifier 10, the shape of the sensor element 2 is constructed so that the sensor element 2 can be inserted on the side of the weft channel between the drop wires 23 and so that the weft stop motion 1 can be attached on the side of the weft channel to the loom sley 22, also within the loom width so that its position can be varied.

Figure 8:
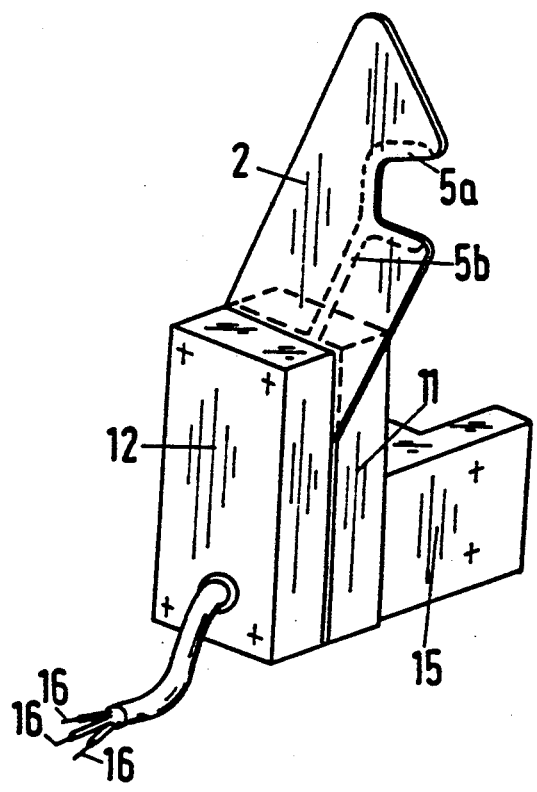
FIG. 8 shows a further perspective representation for a weft break stop motion with an attachment device.

FIG. 8 shows a further embodiment of a sensor element 2 with an attachment device 15, which can be attached on the side of the reed 18 remote from the weft channel 1 to the loom sley 23, also within the loom width, so that its position can be varied.

The attachment device 15 has the additional property that there are devices which enable the feeler 5a in the weft channel 19 of the reed 18 to be positioned so that the sensor element at least partially surrounds the weft channel 19, without protruding into the weft channel 19. The weft stop motion 1 described for air-jet looms is also suitable for other types of looms in which the thread has an electrostatic charge. Thus this weft stop motion is also suitable for projectile weaving machines, for example.

What is claimed is:

1. Apparatus for sensing an electrical charge of a weft thread for installation on a loom, the apparatus comprising a plate-like sensor element defined by at least three layers of a conductive material and insulation material between and separating adjacent layers of the conductive material to thereby define a middle conductive layer and first and second outer conductive layers, means for grounding the outer conductive layers, and means for electrically coupling the middle conductive layer with means for registering an electrical potential, whereby an electric charge of the weft thread located in the vicinity of and spaced from the middle conductive layer can be sensed without physical contact between the weft thread and the middle conductive layer.

2. Apparatus according to claim 1 wherein the conductive layers and the insulation material define an edge of the sensor element in the vicinity of the weft thread, and wherein the sensor element is adapted to be oriented substantially perpendicular to a weft thread insertion direction of the loom.

3. Apparatus according to claim 1 wherein the middle conductive layer of the sensor element is formed to define a feeler having a shape of an open loop.

4. Apparatus according to claim 1 wherein the middle conductive layer of the sensor element is formed to define a feeler having an edge adapted for positioning proximate the weft thread, and wherein the sensor element includes an electrically insulating layer adapted to be positioned between a weft channel of the loom and the feeler.

5. Apparatus according to claim 1 wherein the middle conductive layer of the sensor element is formed to define a feeler having a non-insulated edge for positioning proximate the weft thread.

6. Apparatus according to claim 1 wherein the middle conductive layer of the sensor element is formed to define a feeler having an edge for positioning proximate the weft thread, and including an electrical conductor at the edge electrically conductively coupled to the feeler only.

7. Apparatus according to claim 1 wherein the sensor element includes a printed circuit board constructed in the form of a multi-layered sandwich.

8. Apparatus according to claim 7 wherein the middle conductive layer of the sensor element is formed to define a feeler, wherein the apparatus includes a charge amplifier and means forming an electrical connection between the feeler and the charge amplifier, and wherein the outer conductive layers of the sensor element are arranged to electrically shield the electrical connection means.

9. Apparatus according to claim 8 including a support for the sensor element integrally constructed with the sensor element and forming a unit therewith, wherein the middle conductive layer of the sensor element defines a printed circuit board including a feeler, and wherein the electrical connection between the feeler and the charge amplifier is formed by the circuit board.

10. Apparatus according to claim 9 including at least one electronic component mounted on the printed circuit board, and wherein the circuit board forms an electrical connection coupling the feeler with the at least one other electronic component.

11. Apparatus according to claim 9 wherein the charge amplifier is mounted directly to the printed circuit board and is disposed between the printed circuit board and the insulating material so that the outer conductive layers electrically shield the charge amplifier.

12. Apparatus according to claim 11 including at least one additional electronic component mounted directly to the printed circuit board and is disposed between the printed circuit board and the insulating material so that the outer conductive layers electrically shield the at least one additional electronic component.

13. Apparatus according to claim 8 including a support for the sensor element integrally constructed with the sensor element and forming a unit therewith, an electrically shielding housing placed over the support, the charge amplifier being disposed inside the housing, wherein electrical connections between the feeler and the charge amplifier and additional electronic components of the apparatus are formed by a sub-region of the shielded outer conductive layer, and wherein the middle conductive layer including the feeler is connected through the insulating material to the sub-region of the shielded outer conductive layer.

14. Apparatus according to claim 13 including at least one further electronic component dispose inside the housing, and wherein the electrical connection between the feeler and the at least one further electronic component is formed by a sub-region of the outer conductive layer and extends through the insulating material between the outer conductive layer and the middle conductive layer.

15. A loom comprising a detector for sensing an electrical charge of a weft thread inserted in the loom, the detector including a plate-like sensor element defined by at least three layers of a conductive material and insulation material between and separating adjacent layers of the conductive material to thereby define a middle conductive layer and first and second outer conductive layers, means for grounding the outer conductive layers, and means for electrically coupling the middle conductive layer with means for registering an electrical potential, whereby an electric charge of the weft thread located in the vicinity of and spaced from the middle conductive layer can be sensed without physical contact between the weft thread and the middle conductive layer.

16. A loom according to claim 15 wherein the loom includes a reed having drop wires, and wherein the detector is at least partially disposed between the drop wires.

17. A loom according to claim 16 including means for attaching the detector to the reed.

18. A loom according to claim 17 wherein the attachment means includes means for varying the position of the detector along the reed.

19. A loom according to claim 18 wherein the attachment means positions the sensor element outside a loom width.

20. A loom according to claim 15 including a loom sley, and means for attaching the detector to the sley.

* * * * *